(12) United States Patent
Larsen et al.

(10) Patent No.: US 9,048,521 B2
(45) Date of Patent: Jun. 2, 2015

(54) BROADBAND WAVEGUIDE

(75) Inventors: Christopher George Larsen, Cincinnati, OH (US); Richard Allan Roth, II, Goshen, OH (US); Stuart James Shelley, Cincinnati, OH (US); Aaron Collins Hacker, Cincinnati, OH (US); Adam Jacob Hehr, Port Clinton, OH (US)

(73) Assignee: Etegent Technologies, Ltd., Cincinnati, OH (US)

( * ) Notice: Subject to any disclaimer, the term of this patent is extended or adjusted under 35 U.S.C. 154(b) by 1014 days.

(21) Appl. No.: 13/071,159

(22) Filed: Mar. 24, 2011

(65) Prior Publication Data

US 2012/0242426 A1    Sep. 27, 2012

(51) Int. Cl.
| | |
|---|---|
| *H01P 3/00* | (2006.01) |
| *H01P 5/00* | (2006.01) |
| *H01P 3/06* | (2006.01) |
| *G01N 29/24* | (2006.01) |
| *H01P 5/02* | (2006.01) |
| *H01P 5/08* | (2006.01) |

(52) U.S. Cl.
CPC ............. *H01P 3/06* (2013.01); *Y10T 29/49016* (2015.01); *Y10T 29/49004* (2015.01); *G01N 29/2462* (2013.01); *H01P 5/026* (2013.01); *H01P 5/085* (2013.01)

(58) Field of Classification Search
CPC .... G01D 5/485; G01V 11/002; E21B 47/122; H01P 11/005; H01P 3/06
USPC ............... 333/236, 237, 239, 100; 340/853.1, 340/856.3; 367/81; 385/12
See application file for complete search history.

(56) References Cited

U.S. PATENT DOCUMENTS

| | | | | |
|---|---|---|---|---|
| 801,130 | A | * | 10/1905 | Barclay ........................... 178/45 |
| 2,968,943 | A | | 1/1961 | Statham |
| 3,071,974 | A | | 1/1963 | Peterson |

(Continued)

FOREIGN PATENT DOCUMENTS

| | | |
|---|---|---|
| DE | 2521411 A1 | 11/1976 |
| DE | 10200510011402 A1 | 9/2006 |

(Continued)

OTHER PUBLICATIONS

Kulite, Static-Dynamic Transducer, Jun. 17, 2009 (6 pages).

(Continued)

*Primary Examiner* — Dean Takaoka
*Assistant Examiner* — Alan Wong
(74) *Attorney, Agent, or Firm* — Middleton Reutlinger

(57) ABSTRACT

A broadband waveguide incorporates various reflection suppression techniques to reduce reflections in signals communicated thereby. The waveguide includes one or more filaments that each include a first and second end. A first matrix may be configured proximate the first end(s) while a second matrix may be configured proximate an intermediate location between the first and second ends. A damping material may cover a portion of the filament(s) that extends from the second matrix to the second end(s) (including the second end(s) themselves) and/or the second end(s) of the filament(s) is/are shaped to at least partially suppress reflections of the signal therefrom. When configured with multiple filaments, at least two of the filaments may have differing lengths that extend from the second matrix and also operate to at least partially suppress reflections of a signal.

77 Claims, 4 Drawing Sheets

(56) References Cited

U.S. PATENT DOCUMENTS

| | | | |
|---|---|---|---|
| 3,079,800 A | 3/1963 | Hoar | |
| 3,201,735 A | 8/1965 | Brown et al. | |
| 3,584,327 A | 6/1971 | Murry et al. | |
| 4,149,422 A | 4/1979 | Olsen et al. | |
| 4,165,651 A | 8/1979 | Olsen et al. | |
| 4,165,652 A | 8/1979 | Olsen et al. | |
| 4,336,719 A | 6/1982 | Lynnworth | |
| 4,452,334 A | 6/1984 | Rogers | |
| 4,499,438 A * | 2/1985 | Cornelius et al. | 333/1 |
| 4,603,942 A * | 8/1986 | Chang et al. | 385/100 |
| 4,663,965 A | 5/1987 | Metcalf et al. | |
| 4,667,097 A | 5/1987 | Fasching et al. | |
| 4,743,870 A | 5/1988 | Jen et al. | |
| 4,783,997 A | 11/1988 | Lynnworth | |
| 4,800,316 A | 1/1989 | Ju-Zhen | |
| 5,003,825 A | 4/1991 | Lew | |
| 5,022,014 A | 6/1991 | Kulczyk et al. | |
| 5,159,838 A | 11/1992 | Lynnworth | |
| 5,545,984 A * | 8/1996 | Gloden et al. | 324/207.13 |
| 5,670,720 A | 9/1997 | Clark et al. | |
| 5,713,916 A | 2/1998 | Dias | |
| 5,821,430 A | 10/1998 | Kwun et al. | |
| 5,821,743 A * | 10/1998 | Page et al. | 324/207.13 |
| 5,962,790 A | 10/1999 | Lynnworth et al. | |
| 6,047,602 A | 4/2000 | Lynnworth | |
| 6,081,638 A | 6/2000 | Zhou | |
| 6,281,976 B1 | 8/2001 | Taylor et al. | |
| 6,343,511 B1 | 2/2002 | Lynnworth et al. | |
| 6,413,103 B1 | 7/2002 | Merz et al. | |
| 6,889,552 B2 | 5/2005 | Nguyen et al. | |
| 6,912,907 B2 | 7/2005 | Fujimoto | |
| 6,919,779 B2 * | 7/2005 | Raphalovitz et al. | 333/148 |
| 6,975,179 B2 * | 12/2005 | Harris | 333/125 |
| 7,016,047 B2 | 3/2006 | May | |
| 7,017,415 B2 | 3/2006 | Harrold et al. | |
| 7,162,925 B2 | 1/2007 | Dietrich | |
| 7,258,014 B2 | 8/2007 | Rudkin | |
| 7,454,978 B2 | 11/2008 | Schroeder et al. | |
| 7,952,360 B2 * | 5/2011 | Ganesh | 324/536 |
| 2004/0119552 A1 * | 6/2004 | Wray | 333/22 R |
| 2005/0238301 A1 * | 10/2005 | Russell et al. | 385/113 |
| 2006/0290356 A1 | 12/2006 | Pharn et al. | |
| 2008/0307885 A1 | 12/2008 | Ravitch et al. | |

FOREIGN PATENT DOCUMENTS

| | | |
|---|---|---|
| EP | 0053036 A1 | 6/1982 |
| EP | 0467818 A1 | 1/1992 |
| EP | 1014525 A1 | 6/2000 |
| EP | 1566815 A2 | 8/2005 |
| GB | 2114297 A | 8/1983 |
| JP | 61061027 A | 3/1986 |
| WO | 2007136040 A1 | 11/2007 |

OTHER PUBLICATIONS

Hunter, Gary W., Development and Application of High Temperature Sensors and Electronics, NASA Glenn Research Center, Cleveland, OH (26 pages).
Ned, Alexander A.; Kurtz, Dr. Anthony D.; Masheeb, Fawzia; Beheim, Glenn, Leadless SiC Pressure Sensors for High Temperature Applications, 2001 (6 pages)
Ned, Alexander A.; Kurtz, Anthony D.; Beheim, Glenn; Masheeb, Fawzia; Stefanescu, Sorin; Improved SiC Leadless Pressure Sensors for High Temperature Low and High Pressure Applications; Kulite Semiconductor Products, Inc., presented at the 21st Transducer Workshop, Lexington Park, MD, Jun. 22-23, 2004 (7 pages).
Wijesundara, Muthu, Recent Progress in SiC Sensors and Microsystems for Harsh Environments (19 pages).
Inagaki, K.; Kolosov, O.V.; Briggs, G. A. D.; Wright, O. B.; Waveguide ultrasonic force microscopy at 60 MHz; Applied Physics Letters, vol. 76, No. 14, Apr. 3, 2000 (3 pages).
Schuet, S; Wheeler, K; Timucin, D.; Kowalski, M.; Wysocki, P.; Introduction & Motivation Characterization of Chafing Damage Model Based Inference, Model Based Inference for Wire Chafe Diagnostics, Intelligent Systems Division, NASA Ames Research Center, Moffett Field, California, Aging Aircraft 2009 (30 pages).
Rose, Joseph L., A Baseline and Vision of Ultrasonic Guided Wave Inspection Potential, Journal of Pressure Vessel Technology, Aug. 2002, vol. 124, pp. 273-282.
Neill, Ian T.; Oppenheim, I. J.; Greve, D.W.; A Wire-Guided Transducer for Acoustic Emission Sensing, Sensors and Smart Structures Technologies for Civil, Mechanical, and Aerospace Systems, 2007, Proc. of SPIE vol. 6529 652913-1 (8 pages).
Stobbe, David M., Acoustoelasticity in 7075-T651 Aluminum and Dependence of Third Order Elastic Constants on Fatigue Damage, A thesis Presented to the Academic Faculty, School of Mechanical Engineering, Georgia Institute of Technology, Aug. 2005 (91 pages).
Ali, M.G.S., Analysis of Broadband Piezoelectric Transducers by Discrete Time Model, Egypt. J. Sol., vol. (23), No. (2), (2000), pp. 287-295.
Greve, David W.; Sohn, Hoon; Yue, C. Patrick; Oppenheim, Irving J., An Inductively Coupled Lamb Wave Transducer, IEEE Sensors Journal, vol. 7, No. 2, Feb. 2007, pp. 295-301.
Huang, Bin; Shung, K. Kik, Characterictics of very high frequency with wire target and hydrophone, Institute of Physics Publishing, Journal of Physcis: Conference Series 1 (2004) 161-166.
Hollman, Kyle W.; Holland, Mark R.; Miller, James G.; Nagy, Peter B.; Rose, James H., Effective Ultrasonic transmission coefficient for randomly rough surfaces, J. Acoust. Soc. Am. 100 (2), Pt. 1, Aug. 1996, pp. 832-839.
Kwun, Hegeon; Bartels, Keith A.; Hanley, John J., Effects of tensile loading on the properties of elastic-wave propagation in a strand, J. Acoust. Soc. Am 103 (6), Jun. 1998, pp. 3370-3375.
Nieuwenhuis, J. H.; Neumann, J.; Greve, D.W.; Oppenheim, I.J., Generation and detection of guided waves using PZT wafer transducers, Nov. 2005 (19 pages).
Chaki, S.; Bourse, G., Guided ultrasonic waves for non-destructive monitoring of the stress levels in prestressed steel strands, Ultrasonics 49 (2009) 162-171.
Li, Qiuhua; Lieh, Junghsen; Mayer, A, Large deflection of laminated circular plates with clamed edge and uniform loading, Proc. IMechE vol. 219 Part E: J. Process Mechanical Engineering (2005) (6 pages).
Sheplak, Mark; Dugundji, John, Large Deflections of Clamped Circular Plates Under Initial Tension and Transitions to Membrane Behavior, Journal of Applied Mechanics, 1998 (28 Pages).
Behbahani, Alireza R., Need for Robust Sensors for Inherently Fail-Safe Gas Turbine Engine Controls, Monitoring, and Prognostics, May 7, 2006 through Thursday, May 11, 2006, ISA2006, 52nd International Instrumentation Symposium—Cleveland, OH (37 pages).
Di Scalea, Francesco Lanza; Rizzo, Piervincenzo; Seible, Frieder, Stress Measurement and Defect Detection in Steel Strands by Guided Stress Waves, Journal of Materials in Civil Engineering © ASCE/May/Jun. 2003, pp. 219-227.
Miklowitz, Julius, The Theory of Elastic Waves and Waveguides, North-Holland Series in Applied Mathematics and Mechanics, vol. 22, 1978 (634 pages).
Nagy, Peter B.; Kent, Renee M., Ultrasonic assessment of Poisson's ratio in thin rods, J. Acoust. Soc. Am. 98 (5), Pt. 1, Nov. 1995, pp. 2694-2701.
Konkov, E., Ultrasonic Interferometer for High-Accuracy Linear Measurements, Measurement Science Review, vol. 9, No. 6, 2009, pp. 187-188.
Kurtz, Dr. Anthony D., "Miniature Absolute Pressure Transducer," AFSBIR, Control No. F031-1261 (2003).
Nicholson, N.C. and McDicken, W.N., "Waveguides in medical ultrasonics: effect of waveguide medium upon model amplitude," Ultrasonics 1992 vol. 30, No. 2. (pp. 82-86).
Spratt, William K.; Vetelino, John F.; Lynnworth, Lawrence C., "Torsional Ultrasonic Waveguide Sensor," 2010 IEEE International Ultrasonics Symposium Proceedings (pp. 702-706).
Loveday, Philip W., "Analysis of Piezoelectric Ultrasonic Transducers Attached to Waveguides Using Waveguide Finite Elements," IEEE Transactions on Ultrasonics, Ferroelectrics, and Frequency Control, vol. 54, No. 10, Oct. 2007 (pp. 2045-2051).

(56) References Cited

OTHER PUBLICATIONS

Lee, Jung-Ryul and Tsuda, Hiroshi, "Sensor application of fibre ultrasonic waveguide," Meas. Sci. Technol. 17 (2006) pp. 645-652.
Cegla, F.B.; Cawley, P., "Ultrasonic Waveguides for Remote High Temperature NDT," Non-Destructive Testing Group, Department of Mechanical Engineering, Imperial College London SW7 2AZ, United Kingdom.
Redwood, Martin, Mechanical waveguides; the propagation of acoustic and ultrasonic waves in fluids and solids with boundaries, New York, Pergamon Press. 1960.

* cited by examiner

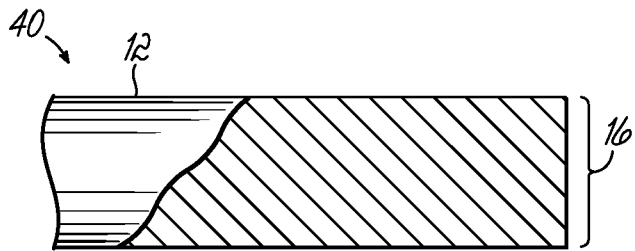
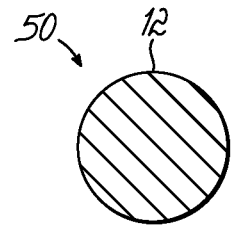
FIG. 3A  FIG. 4A
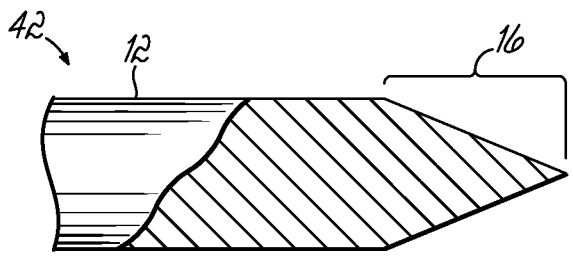
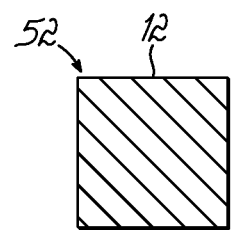
FIG. 3B  FIG. 4B
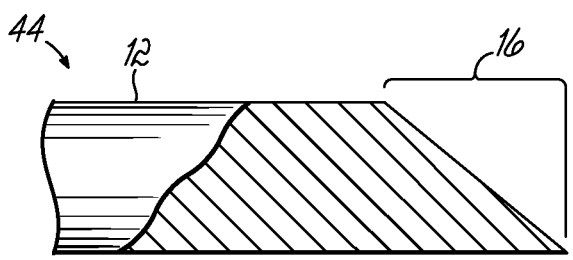
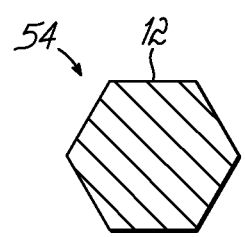
FIG. 3C  FIG. 4C
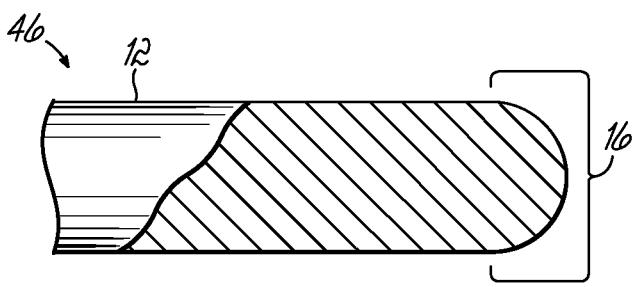
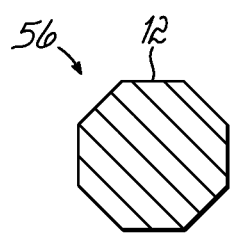
FIG. 3D  FIG. 4D

BROADBAND WAVEGUIDE

GOVERNMENT RIGHTS

Certain aspects of this invention were made with government support under Grant/Contract No. FA8650-09-M-2981 awarded by the Air Force Research Laboratory, Propulsion Directorate. The U.S. Government may have certain rights in the invention.

FIELD OF THE INVENTION

The present invention relates to waveguides for transmitting a signal from proximate one end thereof to an intermediate location thereof.

BACKGROUND OF THE INVENTION

Many conventional mechanical systems are monitored to determine the health thereof and the vibrations caused thereby. However, there are many instances where it is desirable to make broadband measurements of vibration or other physical quantities at locations where it is extremely difficult to do so. For example, the measurement environment may be a harsh environment in which sensors are unable to operate reliably, an environment in which access is so limited that a sensor cannot be physically mounted at the desired location, or an environment in which access is so limited that a sensor cannot be replaced or repaired in the event of failure.

Some conventional methods of dealing with the above issues have generally involved embedding a piezoelectric or strain sensor at the location to be measured and acknowledging that its lifetime and measurement capabilities are limited by the environment within which it is configured. Other conventional methods of dealing with the above issues have involved a mechanical waveguide transmitting a signal at a single, stationary frequency or a signal for which it is unimportant to detect the correct relative phase and/or amplitude of various frequencies. For example, in ultrasonic non-destructive testing of metal die castings, a simple metal rod can act as a waveguide to isolate an ultrasonic sensor from a hot test location, with one end of the rod at the location to be tested and the other end connected to the sensor. As the casting is heated it expands and as the casting cools it shrinks, which can result in cracks within the casting. Each crack, in turn, can be detected using very high frequency (VHF) energy transmitted through the waveguide. However, when the measurement of the actual amplitude and/or phase characteristics of the signal across a frequency band is important rather than the mere detection of cracks using average VHF energy or other techniques using a fixed frequency signal, a traditional waveguide cannot be used, as the ultrasonic signal reflects within the waveguide, resulting in resonances which distort the signal characteristics, making broadband measurements generally impossible.

This drawback of conventional waveguides is that they often have one or more resonant frequencies that in turn causes large peaks and valleys in the spectrum of any signals transmitted thereby. Resonances are often caused by reflections of a signal from the ends of the waveguide. More particularly, a signal initiated at the sensing end of the waveguide travels down the waveguide and reflects off the non-sensing end, then travels back down the waveguide to the sensing end, is reflected off the sensing end back to the non-sensing end, etc. Considered from the perspective of the frequency domain, if there is a periodic signal at a frequency such that the period of the signal is equal to the time it takes for the signal to travel to the end of the waveguide and back to the sensing end, the reflection and the periodic signal will be in phase and re-enforce each other. This creates a standing wave or resonance in the waveguide. The amplitude of the signal response is very large at these frequencies and is very low at intermediate frequencies where the periodic signal and reflected signal cancel each other out rather than re-enforce. This significantly affects sensor readings, rendering detection of a particular signal generally useless.

Consequently, there is a continuing need for improving signal detection with waveguides to address these and other difficulties with conventional waveguide technology.

SUMMARY OF THE INVENTION

Embodiments of the invention are generally directed to a broadband waveguide, as well as methods of making and using same, in which reflections of signal communicated over one or more filaments in such a waveguide are suppressed through one or more unique suppression techniques disclosed herein.

Consistent with one aspect of the invention, multiple filaments in a waveguide may be configured with differing lengths to suppress reflections of a signal communicated by the waveguide. In particular, in some embodiments of the invention, a first matrix is configured proximate the first ends of each of a plurality of filaments, while a second matrix is configured proximate respective intermediate locations between the respective first and second ends of the filaments. However, at least two of the filaments have differing lengths that extend from the second matrix and operate to at least partially suppress reflections of a signal. In such embodiments, the differing lengths of the filaments result in individual components of the reflected signal to add destructively.

Consistent with another aspect of the invention, a damping material may be used to suppress reflections of a signal in one or more filaments in a waveguide. In particular, in some embodiments of the invention, a first matrix is configured proximate the first end of one or more filaments while a second matrix is configured proximate an intermediate location between the first and second ends of the one or more filaments. A damping material covers a portion of one or more of the filaments in the waveguide that extends from the second matrix to the second end to at least partially suppress reflections of the signal from the second end. Additionally and/or alternatively, the second end of one or more of the filaments is shaped to at least partially suppress reflections of the signal from the second end. In some embodiments, for example, the second end may be shaped in a point, wedge, flat angled surface, or dome. In addition, in some embodiments, damping materials and/or shaped ends may be utilized in combination with filaments of differing lengths to further suppress signal reflections.

In one embodiment, a broadband waveguide configured to communicate a signal comprises a plurality of filaments each including a first end, a second end, and a length between the first and second ends, at least two filaments of the plurality of filaments having differing lengths. The waveguide further comprises a first matrix coupling the plurality of filaments to one another proximate the respective first ends thereof and a second matrix coupling the plurality of filaments to one another proximate an intermediate location between the first and second ends thereof, the first and second matrices configured to secure the filaments in a bundle, wherein the at least two filaments having differing lengths operate to suppress reflections of a signal introduced proximate the first matrix caused by the respective second ends.

In another embodiment, a broadband waveguide configured to communicate a signal comprises a filament including a first end, a second end, and a length between the first and second ends, and a matrix coupled to an intermediate location of the filament between the first and second ends thereof. The waveguide further comprises a damping material coupled between the intermediate location and the second end, the damping material configured to at least partially suppress reflections of a signal introduced proximate the first end caused by the second end.

In still another embodiment, a broadband waveguide configured to communicate a signal comprises a filament including a first end, a second end, and a length between the first and second ends, and a matrix coupled to an intermediate location of the filament between the first and second ends thereof, the second end shaped to at least partially suppress reflections of a signal introduced proximate the first end caused by the second end.

Additional embodiments include a broadband waveguide configured to communicate a signal. The waveguide comprises a filament including a first end, a second end, and a length between the first and second ends, and a sensor coupled proximate an intermediate location of the filament between the first and second ends thereof to measure a signal introduced proximate the first end and transmitted along the filament. The waveguide further comprises a damping material coupled between the intermediate location and the second end, the damping material configured to at least partially suppress reflections of the signal caused by the second end.

Still another additional embodiment includes a broadband waveguide configured to communicate a signal that comprises a filament including a first end, a second end, and a length between the first and second ends, and a sensor coupled proximate an intermediate location of the filament between the first and second ends thereof to measure a signal introduced proximate the first end and transmitted along the filament, the second end shaped to at least partially suppress reflections of the signal caused by the second end.

In yet another embodiment, a broadband waveguide configured to communicate a signal comprises a plurality of filaments each including a first end, a second end, and a length between the first and second ends, a first matrix coupling the plurality of filaments to one another proximate the respective first ends thereof, and a second matrix coupling the plurality of filaments to one another proximate an intermediate location between the first and second ends thereof, the first and second matrices configured to secure the filaments in a bundle, wherein the second end of at least one of the plurality of filaments is shaped to at least partially suppress reflections of the signal therefrom.

A still further embodiment includes a broadband waveguide configured to communicate a signal comprising a plurality of filaments each including a first end, a second end, and a length between the first and second ends, and a first matrix coupling the plurality of filaments to one another proximate the respective first ends thereof. The waveguide further comprises a damping material engaging at least a portion of the plurality of filaments between the intermediate location and the respective second ends thereof to at least partially suppress reflections of a signal introduced proximate the first matrix caused by the respective second ends.

In addition, there are provided methods of assembling the above broadband waveguides consistent with embodiments of the invention.

Still further, a waveguide is provided that comprises a plurality of filaments each including a first end, a second end, and having differing lengths, the plurality of filaments coupled to one another at the respective first ends thereof, the plurality of filaments further coupled to one another at an intermediate location between the first and second ends thereof such that respective second ends of the plurality of filaments extend differing distances from the intermediate location.

Furthermore, a method of using a waveguide of the type that includes a plurality of filaments each including a first end, a second end, and a length between the first and second ends, at least two filaments of the plurality of filaments having differing lengths, the broadband waveguide of the type that further includes a first matrix coupling the plurality of filaments to one another proximate the respective first ends thereof and a second matrix coupling the plurality of filaments to one another proximate an intermediate location between the first and second ends thereof, is provided. The method comprises receiving a signal proximate the respective first ends of the plurality of filaments such that the signal is communicated along the plurality of filaments to the intermediate location and measuring the communicated signal proximate the intermediate location.

These and other advantages will be apparent in light of the following figures and detailed description.

BRIEF DESCRIPTION OF THE DRAWINGS

The accompanying drawings, which are incorporated in and constitute a part of this specification, illustrate embodiments of the invention and, together with a general description of the invention given above and the detailed description of the embodiments given below, serve to explain the principles of the invention.

FIGS. 3A-3D are partial cut-away views that show details of respective ends of a filament of the waveguide of FIG. 1 or FIG. 2;

FIGS. 4A-4D are cross-section views of a filament of the waveguide of FIG. 1 or FIG. 2;

It should be understood that the appended drawings are not necessarily to scale, presenting a somewhat simplified representation of various features illustrative of the basic principles of embodiments of the invention. The specific design features of embodiments of the invention as disclosed herein, including, for example, specific dimensions, orientations, locations, and shapes of various illustrated components will be determined in part by the particular intended application and use environment. Certain features of the illustrated embodiments may have been enlarged or distorted relative to others to facilitate visualization and clear understanding.

DETAILED DESCRIPTION

Embodiments of the invention provide a broadband waveguide and methods of making and using the same, and further incorporating various reflection suppression techniques to reduce reflections in signals communicated by such waveguides.

Consistent with one aspect of the invention, multiple filaments in a waveguide may be configured with differing lengths to suppress reflections of a signal communicated by the waveguide. In those embodiments, each of the filaments includes a first end and a second end. A first matrix is configured proximate the first ends of each of a plurality of filaments, while a second matrix is configured proximate respective intermediate locations between the respective first and second ends of the filaments. However, at least two of the filaments have differing lengths that extend from the second matrix and operate to at least partially suppress reflections of a signal. In such embodiments, the differing lengths of the filaments result in individual components of the reflected signal to add destructively.

Consistent with another aspect of the invention, a damping material may be used to suppress reflections of a signal in a waveguide having one or more filaments. In particular, in some embodiments of the invention, a first matrix is configured proximate the first end of the one or more filaments while a second matrix is configured proximate an intermediate location between the first and second ends of the one or more filaments. A damping material covers or otherwise engages a portion of one or more of the filaments in the waveguide that extends from the second matrix to the second end to at least partially suppress reflections of the signal from the second end. Additionally and/or alternatively, the second end of the one or more of the filaments is shaped to at least partially suppress reflections of the signal from the second end. In some embodiments, for example, the second end may be shaped in a point, wedge, flat angled surface, or dome. In addition, in some embodiments, damping materials and/or shaped ends may be utilized in combination with filaments of differing lengths to further suppress signal reflections.

Figure 1:
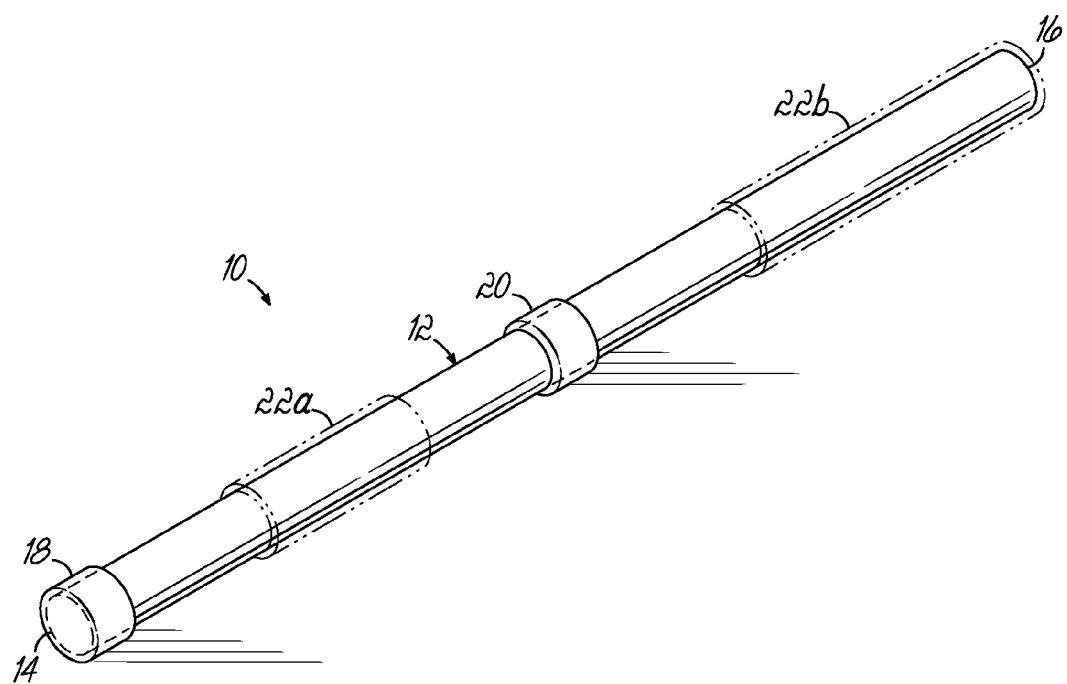
FIG. 1 is a perspective illustration of a broadband waveguide that includes one filament consistent with embodiments of the invention.

FIG. 1 is a perspective illustration of a broadband waveguide 10 consistent with one embodiment of the invention. As illustrated in FIG. 1, the waveguide 10 includes one filament 12 having a first end 14 and a second end 16. The filament 12, in various embodiments, may be configured from metal, plastic, carbon-fiber, or another material that is transmissive of a force signal (e.g., a vibration at a particular frequency range), pressure signal, or other stress wave along at least a portion of the length thereof. The filament 12 may be configured from one material, such as a metal wire (e.g., and thus have a substantially uniform cross-section), or may be configured from two or more materials, such as a clad or sheathed wire (e.g., and thus have a non-uniform cross-section). In those embodiments in which the filament 12 is clad or sheathed, an inner portion (e.g., the "core") may be configured from a first material while an outer portion (e.g., the "cladding) may be configured from a second material. In specific embodiments, the cladding may be metal or a damping material. As such, the cladding may act to prevent noise from being introduced to the core, protect the core from being damaged, protect outside materials from being damaged by the core, and/or for robustness of the filament 12. In those embodiments in which the filament 12 is configured from a metal, the filament 12 of the waveguide 10 may be configured from 0.034" diameter stainless steel wire and have a length of about one meter.

A first matrix 18 is configured proximate the first end 14 of the filament 12 while a second matrix 20 is configured proximate an intermediate location between the first end 14 and the second end 16. As such, at least a portion of the filament 12 extends beyond the second matrix 20 along a longitudinal direction of the filament 12 (e.g., along the length of the filament 12 in the direction from the first matrix 18 to the second matrix 20). The first matrix 18 is configured to provide a material through which to attach the filament 12 to a location (e.g., such as a structure to be monitored). In specific embodiments, the first matrix 18 may be threaded to correspond to a thread at the location. As such, the first matrix 18 may be screwed into the location at which signal measurement is desired. Alternatively, the first matrix 18 may be stud mounted, soldered, welded, brazed, epoxied, adhesed, or otherwise attached to the location at which signal measurement is desired. The second matrix 20 is configured to provide a material through which to sense the signal transmitted through at least a portion of the filament 12 as well as a material upon which to mount a sensor 60 (FIG. 5) to sense the signal transmitted through at least a portion of the filament 12.

In various embodiments, the first matrix 18 and/or the second matrix 20 may be configured from a metal, a frit, an adhesive, an epoxy, a piezo-electric material, or a piezo-resistive material. Additionally and/or alternatively, the first matrix 18 and/or the second matrix 20 may be formed through brazing, welding, or soldering of the filament itself.

In some embodiments, at least a portion of the filament 12, the first matrix 18, and/or the second matrix 20 may be at least partially engaged, covered, or enveloped by a damping material 22a, 22b. More specifically, at least a portion of the filament 12 between the first matrix 18 and the second matrix 20 may be covered or otherwise engaged by the damping material 22a, while the portion of the filament 12 that extends beyond the second matrix 20 may be engaged by the damping material 22b. The damping material 22a may operate to suppress extraneous signals being introduced between the first matrix 18 and the second matrix 20. The damping material 22b, however, operates to suppress reflections of the signal introduced proximate the first matrix 18 from the second end 16 of the filament 12. Suitable damping materials may comprise, for example, rubber, a visco-elastic material, a fluid, batting, ceramic (e.g., for high temperature environments), a tungsten power impregnated epoxy, a heterogeneous metal and plastic mixture, and/or another material that operates to constrain or absorb energy near the second end 16 to mitigate reflections of the signal thereby.

Figure 2:
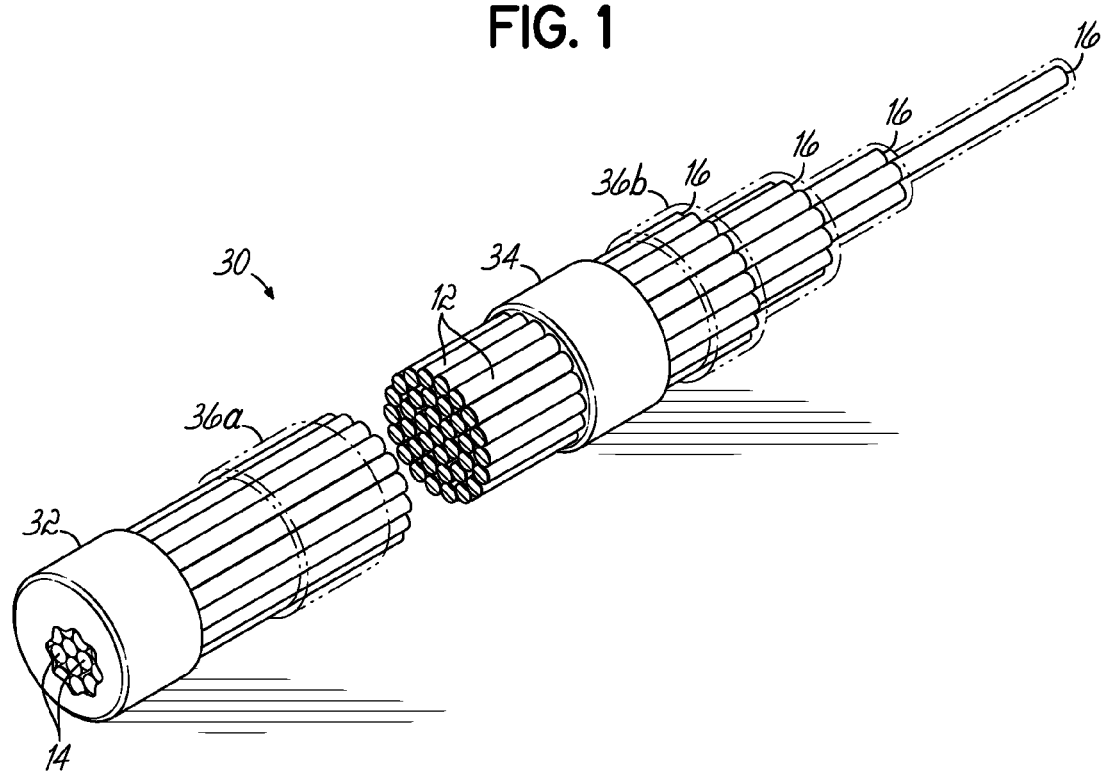
FIG. 2 is a perspective illustration of a broadband waveguide that includes a plurality of filaments consistent with embodiments of the invention.

FIG. 2 is a perspective illustration of another broadband waveguide 30 consistent with an alternative embodiment of the invention. Unlike the waveguide 10 of FIG. 1, the waveguide 30 of FIG. 2 includes a plurality of filaments 12. However, each filament 12 still includes a first end 14 and a second end 16. The plurality of filaments 12 are coupled to one another by way of a first matrix 32 proximate the respective first ends 14 thereof and coupled to one another by way of a second matrix 34 proximate an intermediate location between the respective first ends 14 and second ends 16 thereof. As such, the first matrix 32 and the second matrix 34 are configured to secure the filaments 12 in a bundle. In specific embodiments, the filaments 12 of the waveguide 30 are, again, 0.034" diameter stainless steel wire that are formed, by the first matrix 32 and the second matrix 34, into bundles about 0.25" in diameter. In further specific embodiments, the length of the waveguide 30 is approximately one meter.

Similarly to the first matrix 18 and/or second matrix 20, the first matrix 32 and/or the second matrix 34 may be configured from a metal, a frit, an adhesive, an epoxy, a piezo-electric material, or a piezo-resistive material. Additionally, the first matrix 32 and/or the second matrix 34 may be formed through brazing, welding, or soldering of the filaments themselves.

Similarly to the waveguide 10, at least a portion of the filaments 12, the first matrix 32, and/or the second matrix 34 of the waveguide 30 may be at least partially engaged, covered, or enveloped by a damping material 36a, 36b. More specifically, at least a portion of the filaments 12 between the first matrix 32 and the second matrix 34 may be engaged by the damping material 36a, while the portions of the filaments 12 that extend beyond the second matrix 34 may be engaged by the damping material 36b.

In some embodiments, at least two filaments 12 in the waveguide 30 that have portions that extend beyond the second matrix 34 have differing lengths. These differing lengths operate to suppress reflections of a signal introduced proximate the first matrix 32 from the respective second ends 16 of the filaments 12. More specifically, the reflected signals from the respective second ends 16 of the at least two filaments 12 are generally at a different phase of the signal such that, when combined, the individual components of the reflected signals do not add constructively. As illustrated in FIG. 2, four sets of filaments 12 have portions that extend beyond the second matrix 34. In particular, each filament 12 within a set has the same length, while each set of filaments 12 has a length that differs from the other sets of filaments 12. In alternative embodiments, each of a plurality of filaments 12 in the waveguide 30 has a portion that extends beyond the second matrix 34 with a length that differs from each other filament 12 in the waveguide 30.

To further suppress reflections of the signal introduced proximate the first matrix 18 or 32, the second end 16 of a filament 12 in the waveguide 10 or 30 may be configured with a particular geometry. More specifically, FIG. 3A is an illustration 40 of a conventional second end 16 of a filament 12. As illustrated in FIG. 3A, the second end 16 is substantially flat and substantially orthogonal to the longitudinal direction of travel of the signal in the filament 12. Thus, when the signal reaches the second end 16, it has a relatively strong reflection from the flat surface of the second end 16. However, an alternative configuration for a second end 16 may be used to suppress reflections of the signal from the second end 16.

FIGS. 3B-3D illustrate three alternative configurations for a second end 16 consistent with embodiments of the invention. Specifically, FIG. 3B is an illustration 42 of a cross section of a substantially conical, pyramidal, or tapered (e.g., pointed or wedged) second end 16; FIG. 3C is an illustration 44 of an angled or single-tapered second end 16 (e.g., a substantially flat and angled second end 16); and FIG. 3D is an illustration 46 of a hemi-spherical or dome-shaped second end 16. In operation, the geometries of the second ends 16 of FIGS. 3B-3D operate to change the angle at which the signal interacts with the respective second ends 16 and thus the amount and/or intensity of the reflected signal. More specifically, the geometries of the second ends 16 of FIGS. 3B-3D may cause reflections of the signal to be at different phases such that, when combined, the individual components of the reflected signals do not add constructively. It will be appreciated that filaments may have other end geometries consistent with the invention.

FIGS. 4A-4D illustrate various cross sections of filaments 12 consistent with embodiments of the invention. In some embodiments, the filament 12 may have a conventional and substantially circular cross section as illustrated in cross-section 50 of FIG. 4A. In alternative embodiments, the filament 12 may have an alternative cross-section, such as a substantially tetragonal cross section c (e.g., square, rectangular) as illustrated in cross-section 52 of FIG. 4B, a substantially hexagonal cross section as illustrated in cross-section 54 of FIG. 4C, or a substantially octagonal cross section as illustrated in cross-section 56 of FIG. 4D. It will be appreciated that filaments may have other cross sections consistent with the invention.

Figure 5:
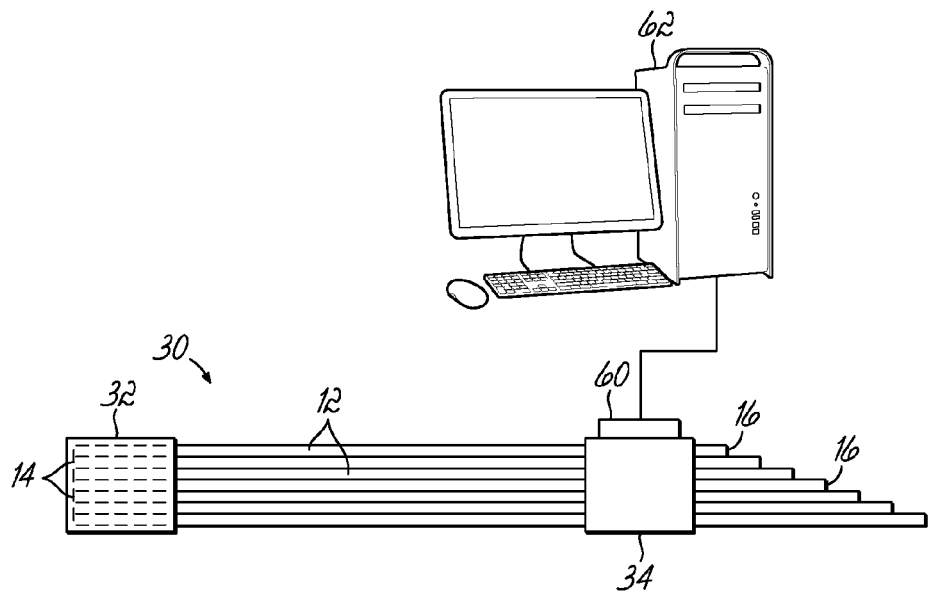
FIG. 5 is an illustration of a computing system coupled to a sensor that, in turn, is coupled to the waveguide of FIG. 2.

In operation, the waveguides 10, 30 transmit a signal introduced proximate the respective first matrices 18, 32 to the respective second matrices 20, 34 for measurement. In particular, and as illustrated in FIG. 5, at least a portion of the second matrix 34 may be machined to receive a sensor 60. The sensor 60, which may be a strain sensor, piezoelectric sensor, accelerometer, motion sensor, load meter, or other force sensor, is then coupled to the second matrix 34 to measure axial strain, radial strain, and/or surface motion of the filaments 12 of the waveguide 30. A computing system 62 is coupled to the sensor 60 to store and/or analyze the signal detected by the sensor 60. Although not shown, it will be appreciated that at least a portion of the second matrix 20 of the waveguide 10 may also be machined to receive the sensor 60 such that the sensor can measure the axial strain, radial strain, and/or surface motion of the filament 12 thereof.

Waveguides 10, 30 consistent with embodiments of the invention may be used for broadband vibration or pressure measurement in hostile environments (e.g., environments with extremely high or low temperatures, corrosive fluids or gases, risks of mechanical damage, high electromagnetic fields) in which the sensor 60 cannot operate reliably and efficiently. Such hostile environments may include environments associated with aircraft (e.g., in the engines thereof, such as to measure vibrations of bearings thereof or to measure pressure inside combustion chambers thereof), pumping systems, marine propulsion, land propulsion, power generation, fan systems, blower systems, boilers, and/or other machinery associated with hazardous fluids or harsh or inaccessible locations, such as steel furnaces, nuclear facilities, wastewater treatment plants, and liquid natural gas processes. Moreover, the waveguides 10, 30 may be used for broadband vibration or pressure measurement in otherwise inaccessible environments, such as sealed compressors or for health monitoring of large structures such as buildings and bridges, as they can be imbedded in concrete to reach supports, anchors, rebar, etc., while having the second matrices 20, 34 thereof in a convenient location for easy replacement of the sensor 60 attached thereto.

Moreover, waveguides 10, 30 are configured to mitigate any low-frequency cutoff. Specifically, it is postulated that the six degree-of-freedom excitation typically found at the location of a structure being interfaced with the respective first matrix 18 or 32 of the respective waveguide 10, 30 causes the filament(s) 12 thereof to undergo bending stress (e.g., the filament(s) 12 "wag" with the location as it vibrates). This dynamic bending stress initiates stress waves that are transmitted to the respective second matrix 20, 34 and may be detected by a sensor 60. As such, low frequency stress waves are created in the filament(s) 12, rather than entering the filament(s) 12 at the first matrix 18, 32, thus bypassing any aperture or low-frequency cutoff issue. This is advantageous for most monitoring applications, as good bandwidth is desirable while resolving a six degrees-of-freedom issue is not important for health monitoring.

Returning to FIG. 1, in any event, and consistent with some embodiments of the invention, the waveguide 10 is used to transmit a signal, such as a force signal, pressure signal, or other stress wave, along the filament 12. The signal is introduced proximate the first matrix 18 and transmitted along the filament 12 to the second matrix 20. As the signal travels down the filament 12 it causes both axial and radial strain. These strains, or the surface motion of the filament 12 caused by these strains, may then be measured by the sensor 60 at the second matrix 20. The damping material 22 and/or the geometry of the second end 16 of the filament 12, in turn, suppress reflections of the signal detected by the sensor 60. This allows a higher fidelity measurement of the signal transmitted along the filament 12 because standing waves or resonances of the signal within the waveguide 10 are at least partially prevented.

Returning to FIG. 2, and consistent with other embodiments of the invention, the waveguide 30 is also used to transmit a signal, such as a force signal, pressure signal, or other stress wave, along the filaments 12. The signal is introduced proximate the first matrix 32 and transmitted along the filaments 12 to the second matrix 34. As the signal travels down the filaments 12 it causes both axial and radial strain, and may cause surface motion of the filaments 12. These strains, or the surface motion of the filaments 12 caused by these strains, may then be measured by the sensor 60 connected to the second matrix 34. The damping material 36, geometry of second ends 16 of the filaments 12, and/or differing lengths of at least two of the filaments 12, in turn, suppress reflections of the signal detected by the sensor 60. This allows a higher fidelity measurement of the signal transmitted along the filaments 12 because standing waves or resonances of the signal within the waveguide 30 are at least partially prevented.

Figure 6:
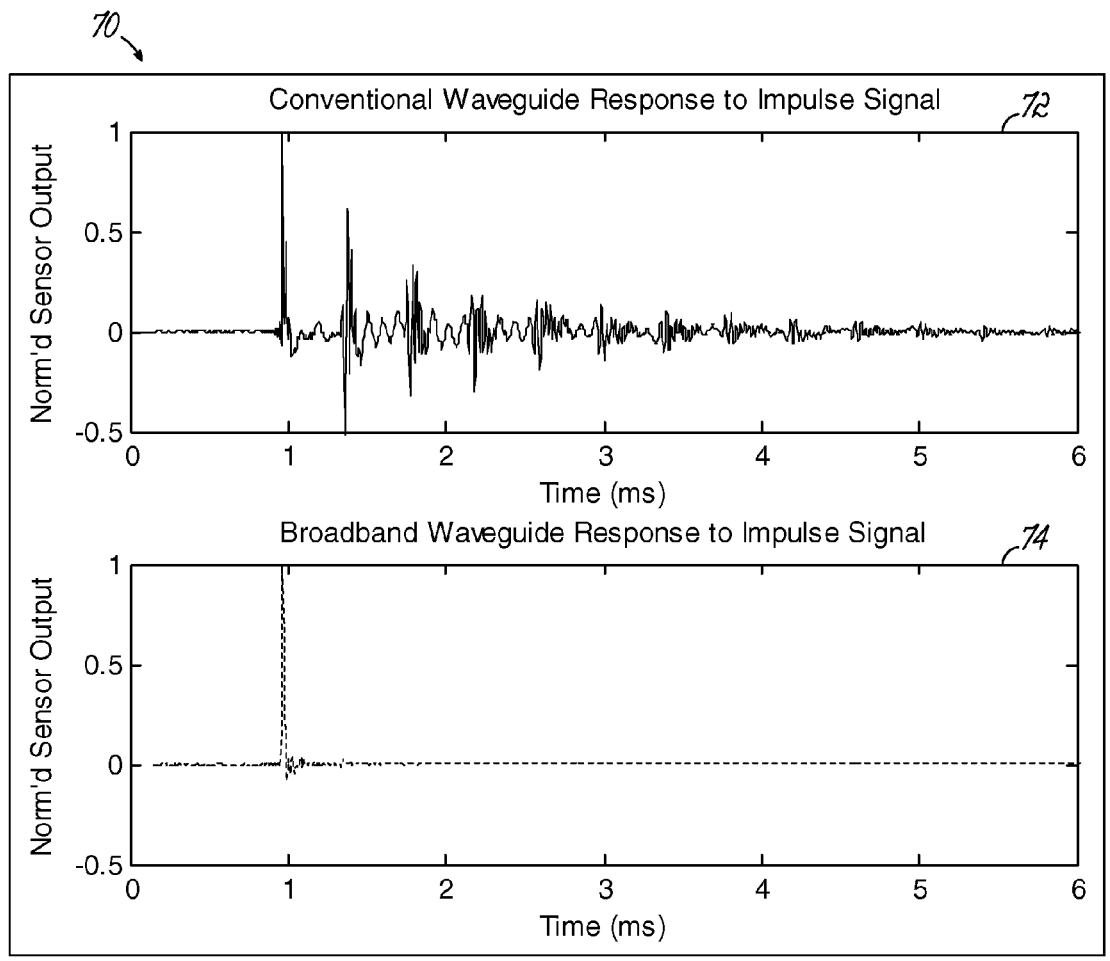
FIG. 6 is an illustration showing a pulse signal as measured by a conventional waveguide versus a pulse signal as measured by an exemplary broadband waveguide similar to those of FIG. 1 or FIG. 2.

FIG. 6 is an illustration 70 showing an exemplary demonstration of the difference of a signal in the form of a pulse as measured by a conventional waveguide versus a pulsed signal as measured by a waveguide similar to the waveguide 10 or 30. When using the conventional waveguide, the signal may first be received at T=1, then reflected within that conventional waveguide. This, in turn, results in significant noise caused by the reflection of the signal. This noise is represented by exemplary spikes in the measurements over time as illustrated in graph 72. However, when using a waveguide similar to the waveguide 10 or 30, as illustrated in graph 74, the signal may not be significantly reflected therein. As such, the signal as measured by a waveguide similar to the waveguide 10 or 30 is centered substantially around a single pulse at T=1, but otherwise does not exhibit significant noise.

Figure 7:
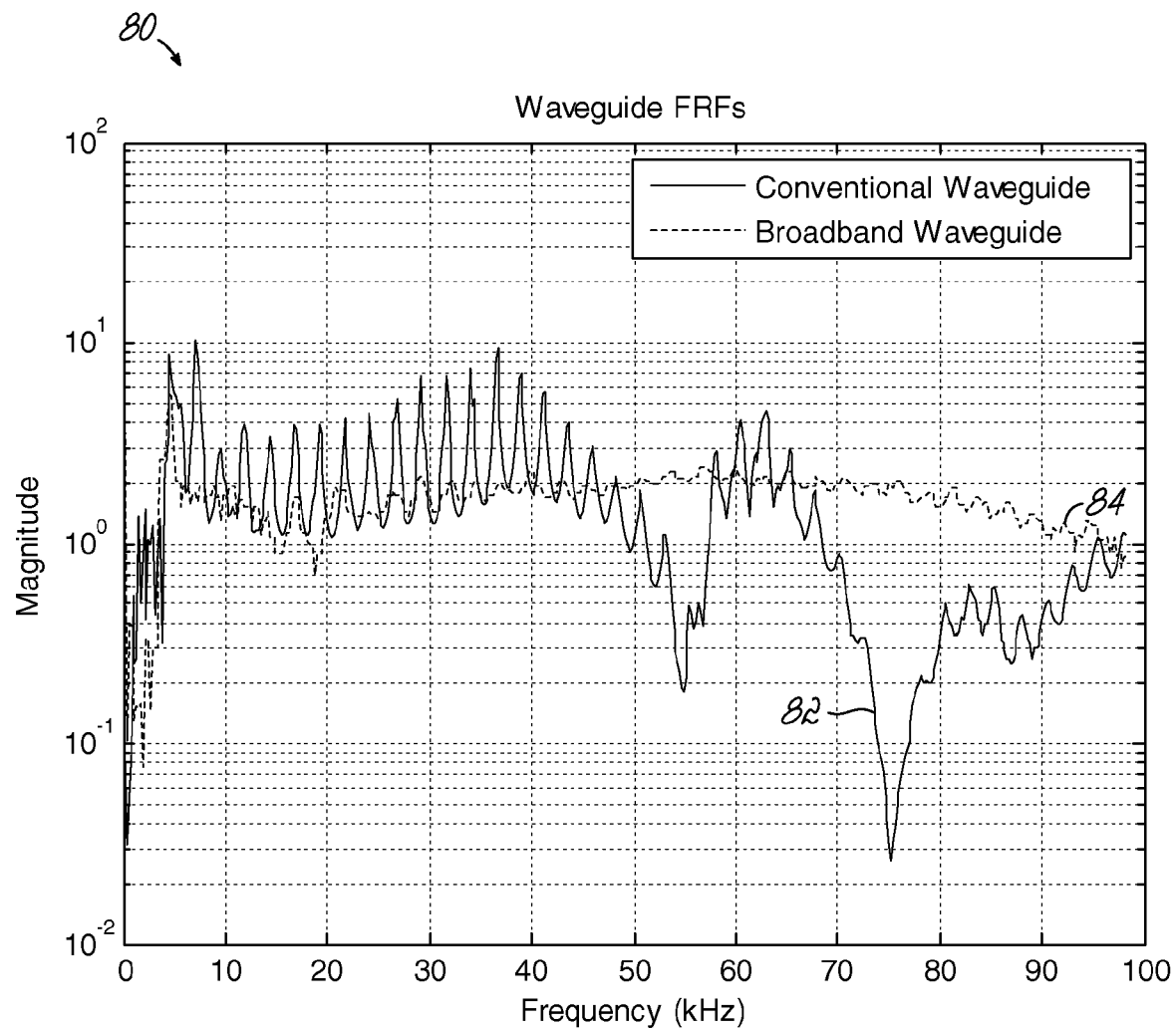
FIG. 7 is a graph illustrating a frequency response function of a conventional waveguide versus a frequency response function of an exemplary broadband waveguide similar to those of FIG. 1 or FIG. 2.

FIG. 7 is a graph 80 illustrating an exemplary frequency response function of a conventional waveguide as at 82 (solid line) versus an exemplary frequency response function of a waveguide similar to the waveguide 10 or 30 as at 84 (dashed line). The frequency response functions 82, 84 may be generated by a multi-frequency signal having a target magnitude (e.g., a magnitude that forms the baseline for the signal, and designated as one). The magnitudes of the signal as measured through the conventional waveguide and the waveguide similar to the waveguide 10 or 30 may then be evaluated with respect to the input signal to determine the respective frequency response functions 82, 84. Each frequency response function 82, 84 is a complex ratio (amplitude and phase) of the sensed signal (e.g. magnitude of the signal as measured through the waveguide 10, 30) to the input signal (e.g. signal input at first end 14 or first matrix 18, 32). Generally, a frequency response function for an ideal waveguide would be flat, meaning it would not vary with frequency, as variation with regard to frequency is a distortion of the measurement quality and quantity. As illustrated in FIG. 7, the exemplary conventional waveguide frequency response function 82 includes many peaks and valleys that may be caused by reflections and/or resonances. As such, the conventional waveguide causes severe distortion in a multi-frequency signal. However, the waveguide similar to the waveguide 10 or 30 has a frequency response function 84 that is relatively flat and exhibits good responses throughout the frequency range of the multi-frequency signal without substantial peaks and valleys caused by reflections/resonances therein.

While the present invention has been illustrated by a description of the various embodiments and the examples, and while these embodiments have been described in considerable detail, it is not the intention of the applicants to restrict or in any way limit the scope of the appended claims to such detail. Additional advantages and modifications will readily appear to those skilled in the art. For example, embodiments of the invention that utilize multiple filaments 12 in a waveguide may include more or fewer filaments 12 than those shown and described, but will always include at least two filaments 12. Moreover, embodiments of the invention that utilize multiple filaments 12 in a waveguide may also have sets of one or more filaments 12 with the same lengths, with each filament in a set having a different length from filaments in the other sets. Still further, embodiments of the invention that utilize multiple filaments 12 in a waveguide may utilize filaments 12 that have different lengths from one another. Finally, embodiments of the invention that utilize multiple filaments 12 in a waveguide may utilize filaments 12 having the same lengths but being engaged by a damping material 22a, 22b, include alternatively shaped second ends 16 for the filaments 12, and/or include filaments 12 having alternative cross-sections.

By way of further example, embodiments of the invention that utilize one filament 12 in a waveguide may not include the first matrix 18. In those embodiments, the first end 14 of the filament 12 may be coupled directly to the location to be measured (e.g., fixedly or removably, such as welded to the location, threaded into a hole at the location, or otherwise coupled to the location). Moreover, embodiments of the invention that utilize one filament 12 in a waveguide may not include the second matrix 20. In those embodiments, the sensor 60 may be coupled to the filament 12 at the intermediate location. Furthermore, alternatively shaped second ends 16 for filaments 12 may be used other than those illustrated and described and filaments 12 having more or fewer surfaces (e.g., having more or fewer sides in the cross-section thereof) may be used other than those illustrated and described. By way of further example, alternatively shaped second ends 16 may be non-linear cones or have graduated and defined diameters in a stepped fashion. Also by way of further example, alternatively shaped cross-sections for a filament 12 may include non-radially symmetric cross sections, elliptical cross-sections, and rectangular cross-sections, to name a few. A multi-filament waveguide may also include multiple types of filaments such that multiple filament cross-sections and/or multiple filament end geometries may be provided within the same waveguide. Thus, the invention in its broader aspects is therefore not limited to the specific details and representative apparatuses shown and described. Accordingly, departures may be made from such details without departing from the spirit or scope of applicants' general inventive concept.

What is claimed is:

1. A broadband waveguide configured to communicate a signal, comprising:
   a plurality of filaments each including a first end, a second end, and a length between the first and second ends, at least two filaments of the plurality of filaments having differing lengths;
   a first matrix coupling the plurality of filaments to one another proximate the respective first ends thereof; and
   a second matrix coupling the plurality of filaments to one another proximate an intermediate location between the first and second ends thereof, the first and second matrices configured to secure the filaments in a bundle, wherein the at least two filaments having differing lengths operate to suppress reflections of a signal introduced proximate the first matrix caused by the respective second ends.

2. The broadband waveguide of claim 1, wherein the first matrix comprises a metal.

3. The broadband waveguide of claim 1, wherein the first matrix comprises a frit.

4. The broadband waveguide of claim 1, wherein the first matrix comprises an adhesive.

5. The broadband waveguide of claim 1, wherein the first matrix comprises an epoxy.

6. The broadband waveguide of claim 1, wherein the first matrix is formed by brazing the plurality of filaments.

7. The broadband waveguide of claim 1, wherein the first matrix is formed by welding the plurality of filaments.

8. The broadband waveguide of claim 1, wherein the second matrix comprises a metal.

9. The broadband waveguide of claim 1, wherein the second matrix comprises a frit.

10. The broadband waveguide of claim 1, wherein the second matrix comprises an adhesive.

11. The broadband waveguide of claim 1, wherein the second matrix comprises an epoxy.

12. The broadband waveguide of claim 1, wherein the second matrix is formed by brazing the plurality of filaments.

13. The broadband waveguide of claim 1, wherein the second matrix is formed by welding the plurality of filaments.

14. The broadband waveguide of claim 1, wherein the second matrix is a piezoelectric material.

15. The broadband waveguide of claim 14, further comprising:
a voltage sensor coupled to the second matrix, the voltage sensor configured to measure a voltage of the second matrix induced by the signal communicated along the plurality of filaments to the intermediate location.

16. The broadband waveguide of claim 1, further comprising:
a strain sensor proximate the second matrix, the strain sensor configured to measure the signal communicated along the plurality of filaments to the intermediate location.

17. The broadband waveguide of claim 1, further comprising:
a piezoelectric sensor proximate the second matrix, the piezoelectric sensor configured to measure the signal communicated along the plurality of filaments to the intermediate location.

18. The broadband waveguide of claim 1, further comprising:
an accelerometer proximate the second matrix, the accelerometer configured to measure the signal communicated along the plurality of filaments to the intermediate location.

19. The broadband waveguide of claim 1, further comprising:
a load meter proximate the second matrix, the load meter configured to measure the signal communicated along the plurality of filaments to the intermediate location.

20. The broadband waveguide of claim 1, further comprising:
a damping material engaging at least a portion of the plurality of filaments between the first matrix and the second matrix.

21. The broadband waveguide of claim 1, wherein the respective second ends of the at least two filaments are spaced from one another beyond the intermediate location along a longitudinal direction of the at least two filaments.

22. The broadband waveguide of claim 1, further comprising:
a damping material engaging at least a portion of the at least two filaments between the intermediate location and the respective second ends thereof to at least partially suppress reflections of the signal caused by the respective second ends of the at least two filaments.

23. The broadband waveguide of claim 1, the second end of at least one of the plurality of filaments shaped to at least partially suppress reflections of the signal therefrom.

24. The broadband waveguide of claim 23, wherein a first filament of the at least two filaments includes a second end that is substantially flat and substantially orthogonal with respect to a longitudinal direction of the first filament.

25. The broadband waveguide of claim 23, wherein a first filament of the at least two filaments includes a second end that is substantially conical.

26. The broadband waveguide of claim 23, wherein a first filament of the at least two filaments includes a second end that is substantially flat and angled with respect to a longitudinal direction of the first filament.

27. The broadband waveguide of claim 23, wherein a first filament of the at least two filaments includes a second end that is substantially dome-shaped.

28. A broadband mechanical waveguide configured to communicate a stress wave, comprising:
a filament including a first end, a second end, and a length between the first and second ends, the filament formed of a material that is transmissive of stress waves, the first end of the filament configured to be coupled to a structure that generates a stress wave indicative of vibration or pressure at the structure such that the stress wave is introduced proximate the first end of the filament for passive broadband measurement of the vibration or pressure proximate an intermediate location of the filament between the first and second ends;
a matrix coupled to the intermediate location of the filament between the first and second ends thereof; and
a damping material coupled between the intermediate location and the second end, the damping material configured to at least partially suppress reflections of the stress wave introduced proximate the first end caused by the second end.

29. The broadband mechanical waveguide of claim 28, further comprising:
a sensor coupled to the matrix and configured to sense axial strain, radial strain or surface motion of the filament caused by the stress wave introduced proximate the first end of the filament.

30. The broadband mechanical waveguide of claim 28, wherein the matrix is a first matrix, the broadband mechanical waveguide further comprising:
a second matrix coupled proximate the first end.

31. A broadband mechanical waveguide configured to communicate a stress wave, comprising:
a filament including a first end, a second end, and a length between the first and second ends, the filament formed of a material that is transmissive of stress waves, the first end of the filament configured to be coupled to a structure that generates a stress wave indicative of vibration or pressure at the structure such that the stress wave is introduced proximate the first end of the filament for passive broadband measurement of the vibration or pressure proximate an intermediate location of the filament between the first and second ends;

a matrix coupled to the intermediate location of the filament between the first and second ends thereof, the second end shaped to at least partially suppress reflections of the stress wave introduced proximate the first end caused by the second end.

32. The broadband mechanical waveguide of claim 31, further comprising:
a sensor coupled to the matrix and configured to sense axial strain, radial strain or surface motion of the filament caused by the stress wave introduced proximate the first end of the filament.

33. The broadband mechanical waveguide of claim 31, wherein the matrix is a first matrix, the broadband mechanical waveguide further comprising:
a second matrix coupled proximate the first end.

34. The broadband mechanical waveguide of claim 31, further comprising:
a damping material coupled between the intermediate location and the second end, the damping material configured to at least partially suppress the reflections of the stress wave caused by the second end.

35. A broadband mechanical waveguide configured to communicate a stress wave, comprising:
a filament including a first end, a second end, and a length between the first and second ends, the filament formed of a material that is transmissive of stress waves, the first end of the filament configured to be coupled to a structure that generates a stress wave indicative of vibration or pressure at the structure such that the stress wave is introduced proximate the first end of the filament for passive broadband measurement of the vibration or pressure proximate an intermediate location of the filament between the first and second ends;
a sensor coupled proximate the intermediate location of the filament between the first and second ends thereof to passively sense axial strain, radial strain or surface motion of the filament caused by the stress wave introduced proximate the first end and transmitted along the filament; and
a damping material coupled between the intermediate location and the second end, the damping material configured to at least partially suppress reflections of the stress wave caused by the second end.

36. A broadband mechanical waveguide configured to communicate a stress wave, comprising:
a filament including a first end, a second end, and a length between the first and second ends, the filament formed of a material that is transmissive of stress waves, the first end of the filament configured to be coupled to a structure that generates a stress wave indicative of vibration or pressure at the structure such that the stress wave is introduced proximate the first end of the filament for passive broadband measurement of the vibration or pressure proximate an intermediate location of the filament between the first and second ends;
a sensor coupled proximate the intermediate location of the filament between the first and second ends thereof to passively sense axial strain, radial strain or surface motion of the filament caused by the stress wave introduced proximate the first end and transmitted along the filament, the second end shaped to at least partially suppress reflections of the stress wave caused by the second end.

37. The broadband mechanical waveguide of claim 36, further comprising:
a damping material coupled between the intermediate location and the second end, the damping material configured to at least partially suppress the reflections of the stress wave caused by the second end.

38. A broadband mechanical waveguide configured to communicate a stress wave, comprising:
a plurality of filaments each including a first end, a second end, and a length between the first and second ends;
a first matrix coupling the plurality of filaments to one another proximate the respective first ends thereof; and
a second matrix coupling the plurality of filaments to one another proximate an intermediate location between the first and second ends thereof, the first and second matrices configured to secure the filaments in a bundle, wherein the second end of at least one of the plurality of filaments is shaped to at least partially suppress reflections of the stress wave therefrom.

39. A broadband mechanical waveguide configured to communicate a stress wave, comprising:
a plurality of filaments each including a first end, a second end, and a length between the first and second ends, each filament formed of a material that is transmissive of stress waves;
a first matrix coupling the plurality of filaments to one another proximate the respective first ends thereof;
a second matrix coupling the plurality of filaments to one another proximate an intermediate location between the first and second ends thereof, the first and second matrices configured to secure the filaments in a bundle; and
a damping material engaging at least a portion of the plurality of filaments between the intermediate location and the respective second ends thereof to at least partially suppress reflections of a stress wave introduced proximate the first matrix caused by the respective second ends.

40. The broadband mechanical waveguide of claim 39, wherein the second end of at least one of the plurality of filaments is shaped to at least partially suppress a reflection of the stress wave therefrom.

41. A method of assembling a broadband mechanical waveguide of the type that includes a plurality of filaments each including a first end, a second end, and a length between the first and second ends, at least two filaments of the plurality of filaments having differing lengths, and the plurality of filaments formed of a material that is transmissive of stress waves, the method comprising:
coupling the plurality of filaments to one another proximate the respective first ends; and
coupling the plurality of filaments to one another proximate an intermediate location between the first and second ends thereof such that the at least two filaments having differing lengths have respective second ends that extend differing distances from the intermediate location along a longitudinal direction of the at least two filaments to suppress reflections of a stress wave introduced proximate the first matrix caused by the respective second ends.

42. The method of claim 41, wherein coupling the plurality of filaments to one another proximate the respective first ends includes:
soldering the plurality of filaments to one another proximate the respective first ends.

43. The method of claim 41, wherein coupling the plurality of filaments to one another proximate the respective first ends includes:
applying a frit to the respective first ends of the plurality of filaments.

44. The method of claim 41, wherein coupling the plurality of filaments to one another proximate the respective first ends includes:
applying an adhesive to the respective first ends of the plurality of filaments.

45. The method of claim 41, wherein coupling the plurality of filaments to one another proximate the respective first ends includes:
applying an epoxy to the respective first ends of the plurality of filaments.

46. The method of claim 41, wherein coupling the plurality of filaments to one another proximate the respective first ends includes:
brazing the plurality of filaments to one another proximate the respective first ends.

47. The method of claim 41, wherein coupling the plurality of filaments to one another proximate the respective first ends includes:
welding the plurality of filaments to one another proximate the respective first ends.

48. The method of claim 41, wherein coupling the plurality of filaments to one another proximate the intermediate location includes:
soldering the plurality of filaments to one another proximate the respective intermediate locations thereof.

49. The method of claim 41, wherein coupling the plurality of filaments to one another proximate the intermediate location includes:
applying a frit to the respective intermediate locations of the plurality of filaments.

50. The method of claim 41, wherein coupling the plurality of filaments to one another proximate the intermediate location includes:
applying an adhesive to the respective intermediate locations of the plurality of filaments.

51. The method of claim 41, wherein coupling the plurality of filaments to one another proximate the intermediate location includes:
applying an epoxy to the respective intermediate locations of the plurality of filaments.

52. The method of claim 41, wherein coupling the plurality of filaments to one another proximate the intermediate location includes:
brazing the plurality of filaments to one another proximate the respective intermediate locations thereof.

53. The method of claim 41, wherein coupling the plurality of filaments to one another proximate the respective intermediate locations includes:
welding the plurality of filaments to one another proximate the respective intermediate locations thereof.

54. The method of claim 41, wherein coupling the plurality of filaments to one another proximate the intermediate location includes:
applying a piezoelectric material to the plurality of filaments at the respective intermediate locations thereof to bind the plurality of filaments to one another.

55. The method of claim 54, further comprising:
sensing a voltage produced by the piezoelectric material in response to a stress wave introduced to the plurality of filaments proximate the first matrix and transmitted along the plurality of filaments to the intermediate location.

56. The method of claim 41, further comprising:
coupling a strain sensor to a second matrix that couples the plurality of filaments to one another proximate the intermediate location; and
measuring a stress wave introduced to the plurality of filaments proximate the first matrix and transmitted along the plurality of filaments to the second matrix with the strain sensor.

57. The method of claim 41, further comprising:
coupling a piezoelectric sensor to the plurality of filaments proximate the intermediate location; and
measuring a stress wave introduced to the plurality of filaments proximate the first matrix and transmitted along the plurality of filaments with the piezoelectric sensor.

58. The method of claim 41, further comprising:
coupling an accelerometer to the plurality of filaments proximate the intermediate location; and
measuring a stress wave introduced to the plurality of filaments proximate the first matrix and transmitted along the plurality of filaments with the accelerometer.

59. The method of claim 41, further comprising:
coupling a load meter to the plurality of filaments proximate the intermediate location; and
measuring a stress wave introduced to the plurality of filaments proximate the first matrix and transmitted along the plurality of filaments with the load meter.

60. The method of claim 41, further comprising:
applying a damping material to engage at least a portion of the plurality of filaments between the respective first ends and the intermediate location.

61. The method of claim 41, further comprising:
applying a damping material to engage at least a portion of the at least two filaments between the intermediate location and the respective second ends thereof to at least partially suppress reflections of the stress wave caused by the respective second ends of the at least two filaments.

62. The method of claim 41, further comprising:
shaping the second end of at least one of the plurality of filaments to at least partially suppress reflections of the stress wave therefrom.

63. A method of assembling a broadband mechanical waveguide of the type that includes a filament that in turn includes a first end, a second end, and a length between the first and second ends, the filament formed of a material that is transmissive of stress waves, the method comprising:
coupling a matrix proximate an intermediate location between the first and second ends;
coupling the first end of the filament to a structure that generates a stress wave indicative of vibration or pressure at the structure such that the stress wave is introduced proximate the first end of the filament for passive broadband measurement of the vibration or pressure proximate the intermediate location between the first and second ends; and
coupling a damping material proximate the second end to at least partially suppress reflections of the stress wave introduced proximate the first end caused by the second end.

64. The method of claim 63, further comprising:
coupling a sensor to the matrix, the sensor configured to sense axial strain, radial strain or surface motion of the filament caused by the stress wave introduced proximate the first end.

65. A method of assembling a broadband mechanical waveguide of the type that includes a filament that in turn includes a first end, a second end, and a length between the first and second ends, the filament formed of a material that is transmissive of stress waves, the method comprising:
coupling a matrix proximate an intermediate location between the first and second ends;

coupling the first end of the filament to a structure that generates a stress wave indicative of vibration or pressure at the structure such that the stress wave is introduced proximate the first end of the filament for passive broadband measurement of the vibration or pressure proximate the intermediate location between the first and second ends; and configuring the second end to at least partially repress reflections of the stress wave introduced proximate the first end caused by the second end.

66. The method of claim 65, further comprising:
coupling a sensor to the matrix, the sensor configured to sense axial strain, radial strain or surface motion of the filament caused by the stress wave.

67. The method of claim 65, wherein the matrix is a first matrix, the method further comprising:
coupling a second matrix proximate the first end.

68. The method of claim 65, further comprising:
coupling a damping material between the intermediate location and the second to at least partially suppress the reflections of the stress wave caused by the second end.

69. A method of assembling a broadband mechanical waveguide of the type that includes a filament that in turn includes a first end, a second end, and a length between the first and second ends, the filament formed of a material that is transmissive of stress waves, the method comprising:
coupling the first end of the filament to a structure that generates a stress wave indicative of vibration or pressure at the structure such that the stress wave is introduced proximate the first end of the filament for passive broadband measurement of the vibration or pressure proximate an intermediate location between the first and second ends;
coupling a sensor proximate the intermediate location of the filament between the first and second ends thereof to passively sense axial strain, radial strain or surface motion of the filament caused by the stress wave introduced proximate the first end and transmitted along the filament; and
coupling a damping material between the intermediate location and the second end to at least partially suppress reflections of the stress wave caused by the second end.

70. A method of assembling a broadband mechanical waveguide of the type that includes a filament that in turn includes a first end, a second end, and a length between the first and second ends, the filament formed of a material that is transmissive of stress waves, the method comprising:
coupling the first end of the filament to a structure that generates a stress wave indicative of vibration or pressure at the structure such that the stress wave is introduced proximate the first end of the filament for passive broadband measurement of the vibration or pressure proximate an intermediate location between the first and second ends;
shaping the second end to at least partially suppress reflections of the stress wave; and
coupling a sensor proximate the intermediate location of the filament between the first and second ends thereof to passively sense axial strain, radial strain or surface motion of the filament caused by the stress wave introduced proximate the first end and transmitted along the filament.

71. The method of claim 70, further comprising:
coupling a damping material between the intermediate location and the second end to at least partially suppress the reflections of the stress wave caused by the second end.

72. A method of assembling a broadband mechanical waveguide of the type that includes a plurality of filaments each including a first end, a second end, and a length between the first and second ends, each of the plurality of filaments formed of a material that is transmissive of stress waves, the method comprising:
coupling the plurality of filaments to one another proximate an intermediate location between the first and second ends thereof, wherein a second end of at least one of the plurality of filaments is shaped to at least partially suppress reflections of a stress wave introduced proximate the first end caused by the second end.

73. A method of assembling a broadband mechanical waveguide of the type that includes a plurality of filaments each including a first end, a second end, and a length between the first and second ends, each of the plurality of filaments formed of a material that is transmissive of stress waves, the method comprising:
coupling the plurality of filaments to one another proximate the respective first ends;
coupling the plurality of filaments to one another proximate an intermediate location between the first and second ends thereof; and
applying a damping material to engage at least a portion of the plurality of filaments between the respective second ends and the intermediate location, wherein the damping material is configured to at least partially suppress reflections of a stress wave introduced proximate the first end caused by the second end.

74. The method of claim 73, wherein a second end of at least one of the plurality of filaments is shaped to at least partially suppress reflections of the stress wave introduced proximate the first end caused by the second end.

75. A broadband mechanical waveguide, comprising:
a plurality of filaments each including a first end, a second end, and having differing lengths, and each formed of a material that is transmissive of stress waves, the plurality of filaments coupled to one another at the respective first ends thereof, the plurality of filaments further coupled to one another at an intermediate location between the first and second ends thereof such that respective second ends of the plurality of filaments extend differing distances from the intermediate location to suppress reflections of a stress wave introduced proximate the first matrix caused by the respective second ends.

76. A method of using a waveguide of the type that includes a plurality of filaments each including a first end, a second end, and a length between the first and second ends, at least two filaments of the plurality of filaments having differing lengths, the broadband waveguide of the type that further includes a first matrix coupling the plurality of filaments to one another proximate the respective first ends thereof and a second matrix coupling the plurality of filaments to one another proximate an intermediate location between the first and second ends thereof, the method comprising:
receiving a signal proximate the respective first ends of the plurality of filaments such that the signal is communicated along the plurality of filaments to the intermediate location; and
measuring the communicated signal proximate the intermediate location.

77. The method of claim 63, wherein the matrix is a first matrix, the method further comprising:
coupling a second matrix proximate the first end.

* * * * *